(12) United States Patent
Aldecoa

(10) Patent No.: US 6,569,204 B1
(45) Date of Patent: May 27, 2003

(54) BONE TISSUE REGENERATING COMPOSITION

(76) Inventor: Eduardo Anitua Aldecoa, San Antonio, 15, E-01005, Vitoria (ES)

( * ) Notice: Subject to any disclaimer, the term of this patent is extended or adjusted under 35 U.S.C. 154(b) by 0 days.

(21) Appl. No.: 09/647,104

(22) PCT Filed: Jan. 25, 2000

(86) PCT No.: PCT/ES00/00029

§ 371 (c)(1),
(2), (4) Date: Dec. 12, 2000

(87) PCT Pub. No.: WO00/44314

PCT Pub. Date: Aug. 3, 2000

(30) Foreign Application Priority Data

Jan. 26, 2000 (ES) .............................................. 9900148

(51) Int. Cl.$^7$ .................................................. A61F 2/36
(52) U.S. Cl. ............................... 623/23.51; 623/23.56; 623/23.61
(58) Field of Search ................................ 623/16, 23.51, 623/23.57, 23.6, 23.61, 23.62

(56) References Cited

U.S. PATENT DOCUMENTS

| 5,366,507 A | 11/1994 | Sottosanti |
| 5,464,440 A | 11/1995 | Johansson |
| 5,569,308 A | 10/1996 | Sottosanti |
| 5,691,305 A | 11/1997 | Baylink et al. |
| 6,156,311 A | * 12/2000 | Strickland et al. ....... 424/130.1 |

OTHER PUBLICATIONS

Marx et al., "Platelet–rich plasma: Growth factor enhancement for bone graft", Oral Surgery, Oral Medicine, Oral Pathology. vol. 85, No. 6, Jun. 1998.*

Narayanan et al., 37 Cementum Specific Components Which Influence Periodontal Connective Tissue Cells, "Connective Tissue Research, 1995, vol. 33, No. 1–3, pp. 19–21 [341–343].

Marx et al., "Platelet–rich Plasma," Oral and Maxillofacial Sugery, vol., 85, No. 6, Jun. 1998.

* cited by examiner

Primary Examiner—Corrine McDermott
Assistant Examiner—Hieu Phan
(74) Attorney, Agent, or Firm—Browdy and Neimark, P.L.L.C.

(57) ABSTRACT

A composition for use in bone tissue regeneration and a method for its preparation, for application principally, but not exclusively, in the practice of oral surgery. The composition makes use of a gel of plasma rich in growth factors (P.R.G.F.) obtained from blood extracts from the patient undergoing the treatment, facilitating a regeneration of the graft site which is more rapid and effective than the results given by currently known materials and techniques.

18 Claims, No Drawings

BONE TISSUE REGENERATING COMPOSITION

CROSS REFERENCE TO RELATED APPLICATION

The present application is the national stage under 35 U.S.C. 371 PCT/ES00/00029, filed Jan. 25, 2000.

BACKGROUND OF THE INVENTION

1. Field of the Invention

The present invention relates to the regeneration of bone tissue within surgical practice in general, and especially in oral surgical practice, by filling a bone cavity with a graft material which stimulates and accelerates the regeneration.

2. Description of related Art

Until the present moment, various graft materials have been used, and the nature of the material used determines how bone tissue is regenerated.

In this respect, several authors have published studies and reports about the use of different materials and/or compounds for this purpose.

Yarnazaki Y, Oida S, Akimoto Y, Shiosa S in Clin Orthop Related Res (1988: 234; 240–9) refer to the use of a bone-derived morphogenetic protein bound with plaster of Paris (calcium sulphate) for this type of regeneration.

Traditionally, both autologous bone and demineralised bone (DFDBA), either alone or combined with other elements, have been used to constitute graft material for bone cavities within this technique.

Moreover, this type of graft material has also been protected with different barrier materials in order to prevent adjacent tissues encroaching on the graft material.

Various materials have been used as barriers for the aforementioned graft material, the most popular being a poly-tetrafluoroethylene membrane, despite creating problems due to the fact that it is not biodegradable and can cause infections in certain cases. In addition to this, since it is generally used in a solid form, it must be trimmed during surgery to conform to the graft recipient site and then sutured in place.

The U.S. Pat. No. 5,366,507 specifies a composition which combines a graft material based on a mixture of dermineralised bone and calcium sulphate, and a barrier material consisting of calcium sulphate. This composition does not greatly improve upon the previous techniques.

Various studies have shown that the growth factors found in the blood encourage bone formation, especially the growth factors P.D.G.F. and T.G.F.B.

However, the practice of extracting and concentrating such growth factors in an outpatient setting is unknown, as is the clinically observable and measurable effect of these growth factors.

SUMMARY OF THE INVENTION

In a particular embodiment of the present invention, a gel of plasma rich in growth factors (P.R.G.F.) as a graft material for the filling and regeneration of bone in cavities and bone defects, or for regeneration.

The present invention provides a method to obtain and prepare the factor rich plasma for out patient use.

The present invention further provides a method and a composition for the regeneration of bone tissue which represents an improved rate in the regeneration and which may be administered rapidly to the patient.

In yet another embodiment of the present invention, there is provided a kit to be used for the preparation of the P.R.G.F. gel.

Advantageously, the use of P.R.G.F. gel for the regeneration of bone tissue brings acceleration and benefits to the bone regeneration which are greater than those of techniques currently in use, as well as quicker and more predictable healing of the soft tissues, as will become apparent below from the results obtained.

DETAILED DESCRIPTION OF THE INVENTION

The invention provides a method of preparing the aforementioned gel which begins with the extraction of blood from the patient undergoing treatment, minutes before surgery begins and prior to the administration of the anaesthetic. Between 10 and 40 ml was taken from each patient, using 5-ml tubes in which 10% trisodic citrate had been placed to act as an anticoagulant.

The tubes were centrifuged at speeds between 160 and 800 G (according to different procedures which can be applied), for 6 minutes or less (depending on the speed) and at room temperature. The blood separates into the following three basic components:

Red blood cells at the bottom of the tube.

Plasma rich in growth factors (P.R.G.F.) in the middle of the tube, above the red layer.

Plasma poor in growth factors (P.P.G.F.) in the upper part of the tube.

A measure, 1 ml, of the upper P.P.G.F. layer of each 5-ml tube was discarded. The platelets present in this P.P.G.F. were less than 15%, as measured with count n=10.

The factor-rich plasma from the central layer of the tubes was transferred to Eppendorf tubes and to each tube containing 1.2 ml of the P.R.G.F. was added 50 $\mu$l of 10% calcium chloride, such that, with the plasma left in this state, the P.P.G.F. gel formed after a time period of 15 to 25 minutes. The plasma can also be mixed with human thrombin (500 units) and calcium chloride in order to obtain the gel instantly (between 3 and 10 sec) and to allow the possibility of applying it with a syringe.

The gel was used alone to fill bone cavities in need of regeneration, giving optimal results, or with the aid of a conventional barrier material to provide external protection, as will be explained below.

The gel can be combined with other components, such as calcium sulphate, autologous bone, reabsorbable hydroxiapatite tricalcium phosphate, calcium carbonate or other regenerative materials, osteoconductive or osteoinductive.

For the production of the P.R.G.F., the preparation kit will contain a centrifuge, pipettes for the separation of the layers of plasma and a system for blood extraction.

The selection of patients was based on the absence of systematic or localised illnesses which could create counter-indications with the treatment. Consent was obtained from all patients, who were informed of the study. The 20 patients presented a vertical fracture or an advanced periodontal illness which required an extraction, and were chosen because the area of implant would allow a subsequent biopsy without additional discomfort. The patients were randomly divided into a P.R.G.F. treatment group and a control group. The mean age of the P.R.G.F. group was 41 (range: 35–55), 4 patients were men and 6 women. The mean age of the control group was 42 (range: 38–54); 4 were men, 6 women.

Three additional patients (2 men and a woman) required multiple extractions in different mouth locations. In each patient, P.R.G.F. was used for one site but not the other, the type of treatment being assigned to the sites at random. This made it possible to include the best control group as both types of treatment were carried out in the same patient, with the same surgical procedure, identical microbiological conditions and the same surgeon.

All patients received antibiotic treatment; amoxicillin (1.5 g/day) was used. Skin flaps were elevated to allow adequate visibility and to make it possible to close up at the first attempt.

Each site was carefully scraped after extraction. In the 10 patients in the experimental treatment group, the defect sites were filled with P.R.G.F. gel. In 5 of the cases, the plasma was mixed with autologous bone to prevent the skin flap from collapsing. For the control group, the procedure was identical but without using the P.R.G.F. gel. Membranes were not used in either of the groups to exclude the possibility of barrier effects interfering with the possible benefits of P.R.G.F.

Biopsy Technique:

The graft recipient site was biopsied between weeks 10 and 15, depending on the availability of the patient. All biopsies were carried out by an examiner who did not know which treatment had been administered to each defect site. The biopsies were taken with hollow trephine dental drills in the centre of the recipient graft site and to a depth of 3 mm. The bone biopsies were fixed for 48 hours using 10% formalin in 5% formic acid on swabs, and mounted in paraffin wax. From each biopsy 5 mm-thick sections were made and these were stained with haematoxylin and eosin. The stained sections were photographed under bright light. All the biopsies were sent to a laboratory for analysis, without specifying which belonged to the control group and which were from the working group.

Results

The formation of epithelium tissue in all 10 patients treated with P.R.G.F. was evaluated as very good or excellent (much better than what is normally found, and comparatively better than the control group). The regeneration of the treated areas was practically complete in 8 of the 10 cases. The degree of regeneration was evaluated with a periodontal probe and by comparison with the previous defects, which had been photographed. The biopsies of these areas showed mature compact bone with well-organised and morphologically normal trabeculae.

The other two cases treated with P.R.G.F. displayed partial regeneration, presenting connective tissue with badly organised trabeculae in the biopsies. Both patients, a man and a woman, were smokers and presented major defects in three alveolar walls.

There were significant differences in the degree of organisation of the trabeculae between the biopsies taken in week 10 and those taken in week 16, and also depending on the size and shape of the defect site. In patients with major defects treated with P.R.G.F. combined with autologous grafts to avoid the collapse of the skin flaps, greater vestibule-lingual widths were obtained.

In the control group, a homogeneous situation was found in the patients' biopsies: connective tissue filling the greater part of the defect site, in clear contrast with the cases treated with P.R.G.F. All the control group biopsies showed connective tissue and connective tissue containing bone trabeculae.

Mature bone was not found in any of the cases. The status of epithelium formation was rated as normal, showing a significant difference to the cases treated with P.R.G.F.

In the patients with more than one recipient graft site, one treated with P.R.G.F. and the other using the conventional method, the epithelisation of the areas treated with P.R.G.F. was much more rapid. The biopsies of the P.R.G.F. treated areas revealed more mature bone with better-organised trabeculae and greater bone regeneration.

The use of P.R.G.F. provides conditions for more rapid and more effective bone regeneration. This P.R.G.F. gel is easy to handle but must be used without any delay in order to conserve the effectiveness of the growth factors.

Although the optimal dosages have yet to be determined, the use of this technique introduces no risk for the patient, whose blood is used in a short period of time after extraction (30 minutes to 8 hours) and is not mixed with any other component of animal or human origin. At present around 250 patients have been treated with good clinical results.

It has been observed through practice that calcium sulphate is occasionally lacking in consistency when it is prepared for application with sterile biocompatible liquids such as water, saline solutions and local anaesthetic solutions, and this can lead to manipulation difficulties during its application, given that it tends to disintegrate and is very soluble.

Additionally, it is quickly diluted in the blood, thus its efficiency in the regeneration of bone tissue could be improved upon.

Results from laboratory experiments have shown that the use [of tricalcium phosphate] offers significant advantages.

Firstly, by its very nature tricalcium phosphate has a higher calcium content.

Secondly, the behaviour of tricalcium phosphate (putty, supersaturated solution), autologous bone mixed with P.R.G.F. (plasma rich in growth factors), P.R.P. (plasma rich in platelets), P.R.G.F. autologous bone plus tricalcium phosphate, during the treatment in its diluted state is more homogeneous as it provides enough plasticity to make it easier to handle.

Thirdly, the dilution of tricalcium phosphate in blood is more limited, lower than that of calcium sulphate, rendering it more effective as a barrier material.

As was pointed out above, the filler material for the bone cavity can essentially be tricalcium phosphate mixed with gel of plasma rich in growth factors, or other combinations with the condition that the material used as a barrier is tricalcium phosphate.

In particular embodiments of the present invention, other combinations for the filler material have been tested, such as the following (all in combination with tricalcium phosphate):

plasma rich in platelets autologous bone freeze-dried bone mixtures of the above the combination proposed by the present invention makes the tasks in operations for bone tissue regeneration more manageable and easier to complete, and, more importantly, the process of regeneration is quicker than with currently known methods and preparations.

What is claimed is:

1. A composition for the regeneration of bone tissue in a recipient graft site, which is a cavity, wherein the composition comprises a graft material consisting of autologous bone and other filler materials; and optionally a barrier material, said other filler materials comprising a gel of plasma rich in growth factors (P.R.G.F.) obtained directly from a patient's blood, wherein platelets from the blood are activated using 10% calcium chloride, in the absence of added thrombin, said gel occupying, at least partially, the cavity.

2. The composition of claim 1, wherein said plasma gel alone occupies the entire cavity.

3. The composition of claim 1, wherein said plasma gel is mixed with autologous bone alone or combined with calcium sulphate.

4. The composition of claim 1, wherein said plasma gel is mixed with other osteoconductive or osteoinductive regenerative materials.

5. The composition of claim 4, wherein the other osteoconductive or osteoinductive materials comprise calcium sulphate.

6. The composition of claim 4, wherein the other osteoconductive or osteoinductive materials comprise calcium carbonate.

7. The composition of claim 4, wherein the other osteoconductive or osteoinductive materials comprise tricalcium phosphate.

8. The composition of claim 4, wherein the other osteoconductive or osteoinductive materials comprise reabsorbable hydroxyapatite.

9. A kit for the preparation of the composition of claim 1, comprising a centrifuge, pipettes to extract separate layers of plasma, a system for extraction of blood, as well as test tubes, Eppendorf tubes, pipette tips and a heating apparatus set at 37 degrees Celsius.

10. A method of preparing a composition for the regeneration of bone tissue comprising the steps of:
  (a) extracting blood from the patient into tubes for centrifugation to which 10% sodium citrate has been previously added;
  (b) centrifuging the tubes between 160–800 G for about 7 minutes at room temperature to separate the blood into the following constituents of a centrifuged product: red blood cells in a bottom layer; P.R.G.F. in a middle layer; and plasma poor in growth factors (P.P.G.F.) in an upper layer;
  (c) extracting P.R.G.F. from the centrifuged product and transferring the P.R.G.F. to a second set of tubes; and
  (d) adding 10% calcium chloride in the absence of added thrombin to the second set of tubes and waiting a period of time for a gel to form.

11. The method of claim 10, wherein the P.R.G.F. extracted from the centrifuged product may include an upper portion of the bottom layer.

12. The method of claim 10, wherein the blood removed in the extracting step is a quantity of 10–50 ml, and the centrifuging step is performed for 6–8 minutes using tubes of 5–10 ml, and the P.R.G.F. is transferred to the tubes in quantities of 1 ml, and wherein the time for formation of the gel after the step of adding the calcium chloride is 2–20 minutes.

13. The method of claim 10, wherein the blood is extracted from the patient before surgery and prior to administration of anesthesia to the patient.

14. A method of regenerating bone tissue, comprising the steps of:
  (a) filling a bone cavity with a graft material comprising the composition of claim 1 and tricalcium phosphate of various particle sizes; and
  (b) placing a layer of a barrier material over at least a portion of the graft material, wherein said barrier material consists of tricalcium phosphate mixed with a substance selected from the group consisting of P.G.R.F., factors extracted from the P.G.R.F., and bone material.

15. The method of claim 14, wherein said graft material is a mixture of plasma rich in platelets and tricalcium phosphate.

16. The method of claim 14, wherein said graft material is a mixture of autologous bone and tricalcium phosphate and optionally P.R.G.F.

17. The method of claim 14, wherein said graft material is a mixture of freeze-dried bone and tricalcium phosphate.

18. The method of claim 14, wherein said graft material comprises tricalcium phosphate, plasma rich in platelets, autologous bone, P.R.G.F. and freeze-dried bone.

\* \* \* \* \*